(12) United States Patent
Sethi et al.

(10) Patent No.: US 8,398,556 B2
(45) Date of Patent: Mar. 19, 2013

(54) SYSTEMS AND METHODS FOR NON-INVASIVE CONTINUOUS BLOOD PRESSURE DETERMINATION

(75) Inventors: Rakesh Sethi, Vancouver (CA); James Nicholas Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 1008 days.

(21) Appl. No.: 12/242,867

(22) Filed: Sep. 30, 2008

(65) Prior Publication Data

US 2009/0326393 A1    Dec. 31, 2009

Related U.S. Application Data

(60) Provisional application No. 61/077,103, filed on Jun. 30, 2008, provisional application No. 61/077,130, filed on Jun. 30, 2008, provisional application No. 61/077,132, filed on Jun. 30, 2008.

(51) Int. Cl.
*A61B 5/02* (2006.01)

(52) U.S. Cl. .................................................. 600/485

(58) Field of Classification Search ................ 600/485
See application file for complete search history.

(56) References Cited

U.S. PATENT DOCUMENTS

| | | |
|---|---|---|
| 3,835,840 A | 9/1974 | Mount |
| 4,561,447 A | 12/1985 | Kawamura et al. |
| 4,566,463 A | 1/1986 | Taniguchi et al. |
| 4,676,253 A | 6/1987 | Newman |
| 4,729,382 A | 3/1988 | Schaffer |
| 4,830,017 A | 5/1989 | Perry |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,140,990 A * | 8/1992 | Jones et al. .................... 600/480 |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |

(Continued)

FOREIGN PATENT DOCUMENTS

| | | |
|---|---|---|
| EP | 0443267 | 8/1991 |
| EP | 0755221 | 1/1997 |

(Continued)

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

(Continued)

*Primary Examiner* — J. E. Angell

(57) ABSTRACT

According to some embodiments, systems and methods are provided for non-invasive continuous blood pressure determination. In some embodiments, a PPG signal is received and locations of pulses within the PPG signal are identified. An area within a particular pulse is measured. The area may be of just the upstroke, downstroke or the entire pulse. The area may be measured relative to a time-domain axis or a baseline of the pulse. The pulse may be split into multiple sections and the area of each section may be measured. The area of one portion of the pulse may correspond to systolic blood pressure while the area of another portion may correspond to diastolic blood pressure. Empirical data may be used to determine blood pressure from the measured area by applying calibration data measured by a suitable device.

20 Claims, 14 Drawing Sheets

U.S. PATENT DOCUMENTS

| | | | |
|---|---|---|---|
| 5,772,601 A | 6/1998 | Oka | |
| 5,772,602 A | 6/1998 | Sakai | |
| 5,776,071 A | 7/1998 | Inukai | |
| 5,785,659 A | 7/1998 | Caro et al. | |
| 5,791,347 A | 8/1998 | Flaherty et al. | |
| 5,797,395 A | 8/1998 | Martin | |
| 5,797,850 A | 8/1998 | Archibald et al. | |
| 5,810,736 A | 9/1998 | Pail | |
| 5,827,181 A | 10/1998 | Dias | |
| 5,830,131 A | 11/1998 | Caro et al. | |
| 5,832,924 A | 11/1998 | Archibald et al. | |
| 5,833,618 A | 11/1998 | Caro | |
| 5,848,970 A | 12/1998 | Voss | |
| 5,857,975 A | 1/1999 | Golub | |
| 5,873,834 A | 2/1999 | Yanagi et al. | |
| 5,904,654 A | 5/1999 | Wohltmann et al. | |
| 5,941,828 A | 8/1999 | Archibald et al. | |
| 5,964,711 A | 10/1999 | Voss | |
| 6,002,952 A | 12/1999 | Diab | |
| 6,004,274 A | 12/1999 | Nolan | |
| 6,007,492 A | 12/1999 | Goto et al. | |
| 6,011,986 A | 1/2000 | Diab et al. | |
| 6,022,320 A | 2/2000 | Ogura | |
| 6,027,452 A | 2/2000 | Flaherty et al. | |
| 6,027,453 A | 2/2000 | Miwa | |
| 6,027,455 A | 2/2000 | Inukai et al. | |
| 6,045,509 A | 4/2000 | Caro et al. | |
| 6,067,462 A | 5/2000 | Diab | |
| 6,083,171 A | 7/2000 | Ono et al. | |
| 6,095,987 A | 8/2000 | Shmulewitz | |
| 6,135,966 A | 10/2000 | Ko | |
| 6,157,850 A | 12/2000 | Diab et al. | |
| 6,159,157 A | 12/2000 | Archibald et al. | |
| 6,161,038 A | 12/2000 | Schookin et al. | |
| 6,186,954 B1 | 2/2001 | Narimatsu | |
| 6,186,955 B1 | 2/2001 | Baura | |
| 6,190,382 B1 | 2/2001 | Ormsby et al. | |
| 6,196,974 B1 | 3/2001 | Miwa | |
| 6,217,524 B1 | 4/2001 | Orr et al. | |
| 6,227,196 B1 | 5/2001 | Jaffe et al. | |
| 6,228,034 B1 | 5/2001 | Voss et al. | |
| 6,241,661 B1 | 6/2001 | Schluess et al. | |
| 6,241,679 B1 | 6/2001 | Curran | |
| 6,245,022 B1 | 6/2001 | Archibald et al. | |
| 6,251,081 B1 | 6/2001 | Narimatsu | |
| 6,263,222 B1 | 7/2001 | Diab et al. | |
| 6,292,689 B1 | 9/2001 | Wallace | |
| 6,293,915 B1 | 9/2001 | Amano et al. | |
| 6,299,582 B1 | 10/2001 | Brockway et al. | |
| 6,332,867 B1 | 12/2001 | Chen et al. | |
| 6,350,242 B1 | 2/2002 | Doten et al. | |
| 6,371,921 B1 | 4/2002 | Caro | |
| 6,443,905 B1 | 9/2002 | Nissila et al. | |
| 6,463,311 B1 | 10/2002 | Diab | |
| 6,471,646 B1 | 10/2002 | Thede | |
| 6,471,655 B1 | 10/2002 | Baura | |
| 6,506,161 B2 | 1/2003 | Brockway et al. | |
| 6,514,211 B1 | 2/2003 | Baura | |
| 6,524,240 B1 | 2/2003 | Thede | |
| 6,561,986 B2 | 5/2003 | Baura | |
| 6,589,185 B1 | 7/2003 | Archibald et al. | |
| 6,602,199 B2 | 8/2003 | Chen et al. | |
| 6,602,201 B1 | 8/2003 | Hepp et al. | |
| 6,606,511 B1 | 8/2003 | Ali et al. | |
| 6,626,839 B2 | 9/2003 | Doten et al. | |
| 6,631,281 B1 | 10/2003 | Kastle | |
| 6,645,156 B2 | 11/2003 | Oka | |
| 6,658,277 B2 | 12/2003 | Wasserman | |
| 6,684,090 B2 | 1/2004 | Ali et al. | |
| RE38,476 E | 3/2004 | Diab et al. | |
| 6,699,194 B1 | 3/2004 | Diab | |
| 6,767,328 B2 | 7/2004 | Kulik | |
| 6,773,397 B2 | 8/2004 | Kelly | |
| 6,783,498 B2 | 8/2004 | Sackner | |
| 6,816,741 B2 | 11/2004 | Diab | |
| 6,822,564 B2 | 11/2004 | Al-Ali | |
| 6,826,419 B2 | 11/2004 | Diab | |
| 6,827,688 B2 | 12/2004 | Goto et al. | |
| 6,852,083 B2 | 2/2005 | Caro | |
| 6,855,112 B2 | 2/2005 | Kao | |
| 6,863,652 B2 | 3/2005 | Huang et al. | |
| 6,869,403 B2 | 3/2005 | Narimatsu et al. | |
| 6,929,610 B2 | 8/2005 | Forstner | |
| 6,996,427 B2 | 2/2006 | Ali et al. | |
| 7,004,907 B2 | 2/2006 | Banet | |
| 7,043,293 B1 | 5/2006 | Baura | |
| 7,044,918 B2 | 5/2006 | Diab | |
| 7,070,566 B2 | 7/2006 | Medero et al. | |
| 7,074,192 B2 | 7/2006 | Friedman et al. | |
| 7,079,035 B2 | 7/2006 | Bock et al. | |
| 7,087,025 B2 | 8/2006 | Baruch | |
| 7,184,809 B1 | 2/2007 | Sterling | |
| 7,215,984 B2 | 5/2007 | Diab et al. | |
| 7,215,986 B2 | 5/2007 | Diab et al. | |
| 7,252,636 B2 | 8/2007 | Brown | |
| 7,320,030 B2 | 1/2008 | Brown | |
| 7,335,162 B2 | 2/2008 | Eide | |
| 7,376,238 B1 | 5/2008 | Rivas et al. | |
| 7,390,300 B2 | 6/2008 | Inukai | |
| 7,390,301 B2 | 6/2008 | Skrabal | |
| 7,393,327 B2 | 7/2008 | Inukai | |
| 7,400,257 B2 | 7/2008 | Rivas | |
| 7,455,643 B1 | 11/2008 | Li et al. | |
| 7,481,772 B2 | 1/2009 | Banet | |
| 7,485,095 B2 | 2/2009 | Shusterman | |
| 2003/0236465 A1 | 12/2003 | Narimatsu et al. | |
| 2005/0119578 A1* | 6/2005 | Kubo | 600/490 |
| 2005/0148885 A1 | 7/2005 | Tweed et al. | |
| 2005/0251344 A1 | 11/2005 | Appel et al. | |
| 2005/0261594 A1 | 11/2005 | Banet | |
| 2006/0009700 A1 | 1/2006 | Brumfield et al. | |
| 2006/0063992 A1 | 3/2006 | Yu et al. | |
| 2006/0063993 A1 | 3/2006 | Yu et al. | |
| 2006/0079945 A1 | 4/2006 | Libbus | |
| 2006/0206021 A1 | 9/2006 | Diab | |
| 2006/0217614 A1 | 9/2006 | Takala et al. | |
| 2006/0217628 A1 | 9/2006 | Huiku | |
| 2006/0241975 A1 | 10/2006 | Brown | |
| 2006/0285736 A1 | 12/2006 | Brown | |
| 2006/0287603 A1 | 12/2006 | Bartnik et al. | |
| 2007/0066910 A1 | 3/2007 | Inukai et al. | |
| 2007/0083093 A1 | 4/2007 | Diab | |
| 2007/0118045 A1 | 5/2007 | Naghavi et al. | |
| 2007/0225582 A1 | 9/2007 | Diab et al. | |
| 2007/0249467 A1 | 10/2007 | Hong et al. | |
| 2008/0015451 A1 | 1/2008 | Hatib et al. | |
| 2008/0030468 A1 | 2/2008 | Ali et al. | |
| 2008/0033305 A1 | 2/2008 | Hatib et al. | |
| 2008/0132798 A1 | 6/2008 | Hong et al. | |
| 2008/0214903 A1 | 9/2008 | Orbach | |
| 2008/0214942 A1 | 9/2008 | Oh et al. | |
| 2008/0242955 A1 | 10/2008 | Uutela et al. | |
| 2009/0048497 A1 | 2/2009 | Keren | |

FOREIGN PATENT DOCUMENTS

| | | |
|---|---|---|
| EP | 1195132 A1 | 10/2002 |
| GB | 2 356 250 | 5/2001 |
| GB | 2 356 251 | 5/2001 |
| GB | 2 356 252 | 5/2001 |
| JP | 03-231630 | 10/1991 |
| JP | 6142082 A | 5/1994 |
| JP | 07-136136 | 5/1995 |
| JP | 03-225268 A1 | 8/2003 |
| WO | 92/03967 A | 3/1992 |

OTHER PUBLICATIONS

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

International Search Report PCT/IB2009/006137, 3 pages, mailed Dec. 3, 2009.

* cited by examiner

US 8,398,556 B2

SYSTEMS AND METHODS FOR NON-INVASIVE CONTINUOUS BLOOD PRESSURE DETERMINATION

CROSS REFERENCE TO RELATED APPLICATIONS

This application claims the benefit of U.S. Provisional Application Nos. 61/077,103, filed Jun. 30, 2008, 61/077,130, filed Jun. 30, 2008, and 61/077,132, filed Jun. 30, 2008, each of which is hereby incorporated by reference herein in its entirety.

SUMMARY

The present disclosure relates to blood pressure monitoring and, more particularly, the present disclosure relates to non-invasive continuous blood pressure (CNIBP) determination from a photoplethysmograph (PPG) signal.

Blood pressure of a patient may be determined based on pulses in a PPG signal. In one implementation, blood pressure may be determined by, for example, measuring the area under a pulse or a portion of the pulse in the PPG signal. These measurements may be correlated with empirical blood pressure data (corresponding to previous blood pressure measurements of the patient or one or more other patients) to determine the blood pressure (systolic, diastolic and mean arterial pressure). In some implementations, the blood pressure may be determined by looking up the area measurement values in a table (which may be predetermined and stored in a memory) to get corresponding blood pressures. Alternatively, the blood pressure may be determined by using any suitable blood pressure-area mapping equation which is generated based on blood pressure and area measurements associated with one or more patients. For example, actually measured samples may be plotted in a graph that maps blood pressure to area. The graph may be analyzed to generate a linear-best-fit-line approximation, non-linear best fit line approximation or other suitable approximation from which to derive an equation that can be used to determine blood pressure by plugging in an area measurement.

In some embodiments, the area that is used to determine blood pressure may be the total area of a PPG signal pulse measured from a starting point of the pulse to the ending point of the pulse. Alternatively, the area that is used to determine blood pressure may be the area of the upstroke portion of a pulse (e.g., the region starting with the minimum point of the pulse and ending at the maximum point of the pulse) in a PPG signal. Each area that is measured and used to determine blood pressure may be measured relative to a baseline of the pulse (i.e., a line extending from the starting point of the pulse to the ending point of the pulse) or the time-domain axis. In some embodiments, one area of the PPG signal pulse may be used to determine the systolic blood pressure and another area of the PPG signal pulse (i.e., a different portion of the pulse) may be used to determine the diastolic blood pressure.

In some embodiments, the area that is used to determine blood pressure may be measured from two different sections of the PPG signal pulse (e.g., an area of an upper portion of the pulse and an area of a lower portion of the pulse). For example, the pulse may be split into two separate sections (e.g., a top and bottom section) along the time domain axis. Each portion's area may be measured separately. Each portion's area may then be used to either determine the systolic blood pressure or diastolic blood pressure.

In some embodiments, an average, median, maximum, minimum or other suitable function of area may be computed by measuring areas of multiple PPG signal pulses. For example, a first area of a pulse may be measured followed by measuring a second area of a subsequent pulse in the PPG signal. An average may be computed of the two areas of the pulses and used to determine blood pressure by, for example, using empirical data (or a suitable equation representing blood pressure and area) that provides a correspondence between area of a particular patient and blood pressure.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

A PPG signal is typically generated by a pulse oximeter. Pulse oximeters typically measure and display various blood flow characteristics including, but not limited to, the oxygen saturation of hemoglobin in arterial blood. Oximeters pass light through blood perfused tissue such as a finger or an ear, and photoelectrically sense the absorption of light in the tissue. The amount of light absorbed is then used to calculate the amount of the blood constituent (e.g., oxyhemoglobin) being measured.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electro-gastrogram, electromyogram, heart rate signals, pathological sounds, ultrasound, or any other suitable biosignal), or any combination thereof.

This disclosure generally relates to blood pressure determination from a time-domain PPG signal. It should be understood that the received PPG signal may be digital. For illustrative purposes, this disclosure will be described in the context of time-domain PPG signal generated by a pulse oximeter. It should be understood that the PPG signal may also be generated by any other suitable device(s) capable of generating a PPG or any plethysmograph signal.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

Figure 1:
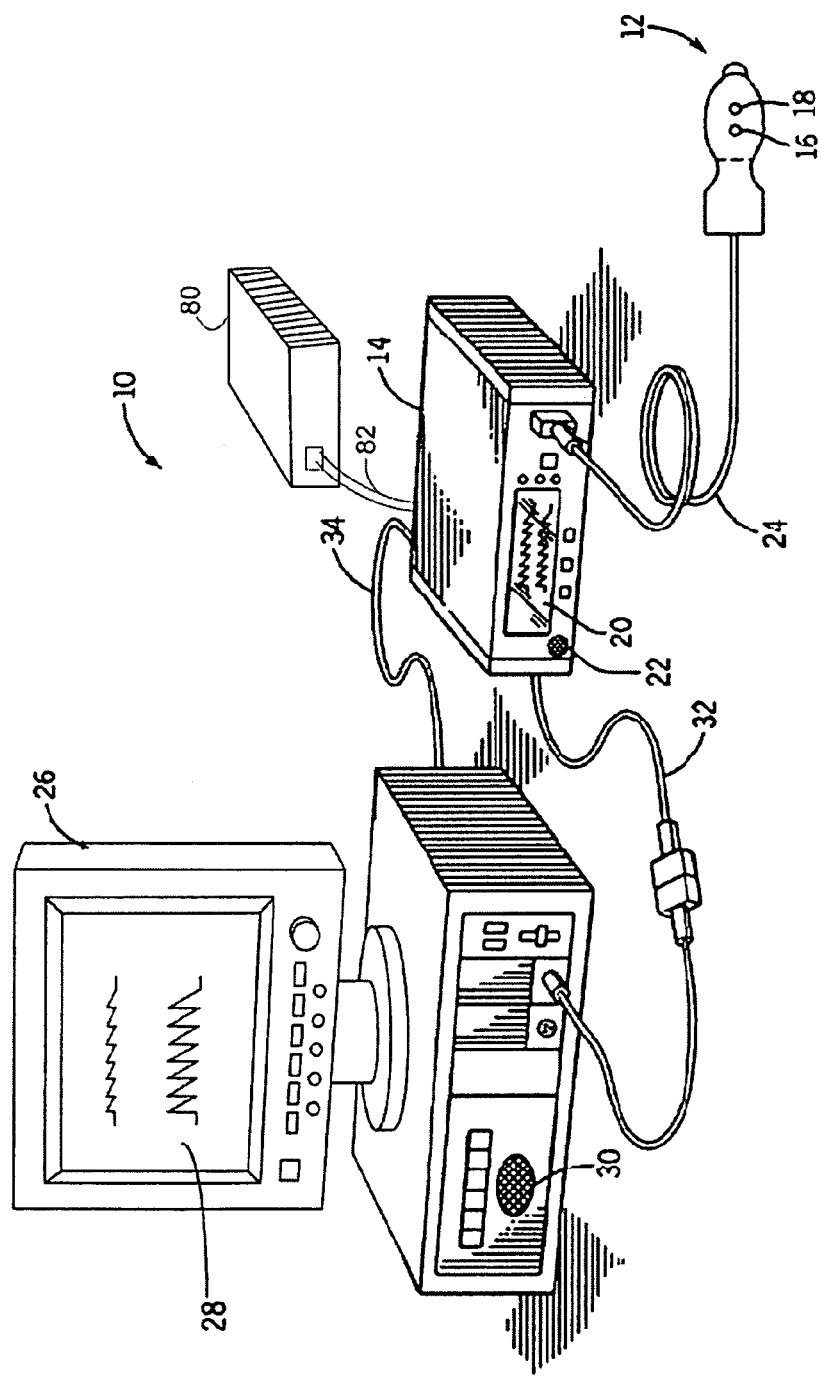
FIG. 1 shows an illustrative CNIBP monitoring system in accordance with an embodiment.

FIG. 1 shows an illustrative CNIBP monitoring system 10 that may also be used to perform pulse oximetry. System 10 may include a sensor 12 and a monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry or CNIBP data from a patient's forehead, neck (carotid artery), wrist (radial artery), inside of a thigh (femoral artery), ankle (tibial artery) or around the ear (in front of the ear). Any other suitable location on a patient's body may be used where emitter 16 and detector 18 may be arranged so that light from emitter 16 penetrates the tissue.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., blood pressure) based at least in part on data received from sensor 12 relating to light emission and detection. In an alternative embodiment, the calculations may be performed on the monitoring device itself and the result of the light intensity reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure from monitor 14, blood oxygen saturation generated by monitor 14 (referred to as an "$SpO_2$" measurement), and pulse rate information from monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury spygmomanometer and occluding cuff, a pressure sensor inserted directly into a suitable artery of a patient, or any other device or mechanism used to sense, measure, determine, or derive a reference blood pressure measurement. In some embodiments, calibration device 80 may include a manual input device (not shown) used by an operator to manually input reference blood pressure measurements obtained from some other source (e.g., an external invasive or non-invasive blood pressure measurement system).

In accordance with some embodiments, the reference blood pressure measurements may be used to generate empirical data for one or multiple patients. In particular, the reference blood pressure measurements may be used to provide coefficient information for the equations generated based on the empirical data that may be used to determine blood pressure based on an area under a pulse of a PPG signal.

Calibration device 80 may also access reference blood pressure measurements stored in memory (e.g., RAM, ROM, or a storage device). For example, in some embodiments, calibration device 80 may access reference blood pressure measurements from a relational database stored within calibration device 80, monitor 14, or multi-parameter patient monitor 26. As described in more detail below, the reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14. Reference blood pressure measurements may then be wirelessly transmitted to monitor 14 for use in calibration. In still other embodiments, calibration device 80 is completely integrated within monitor 14.

Figure 2:
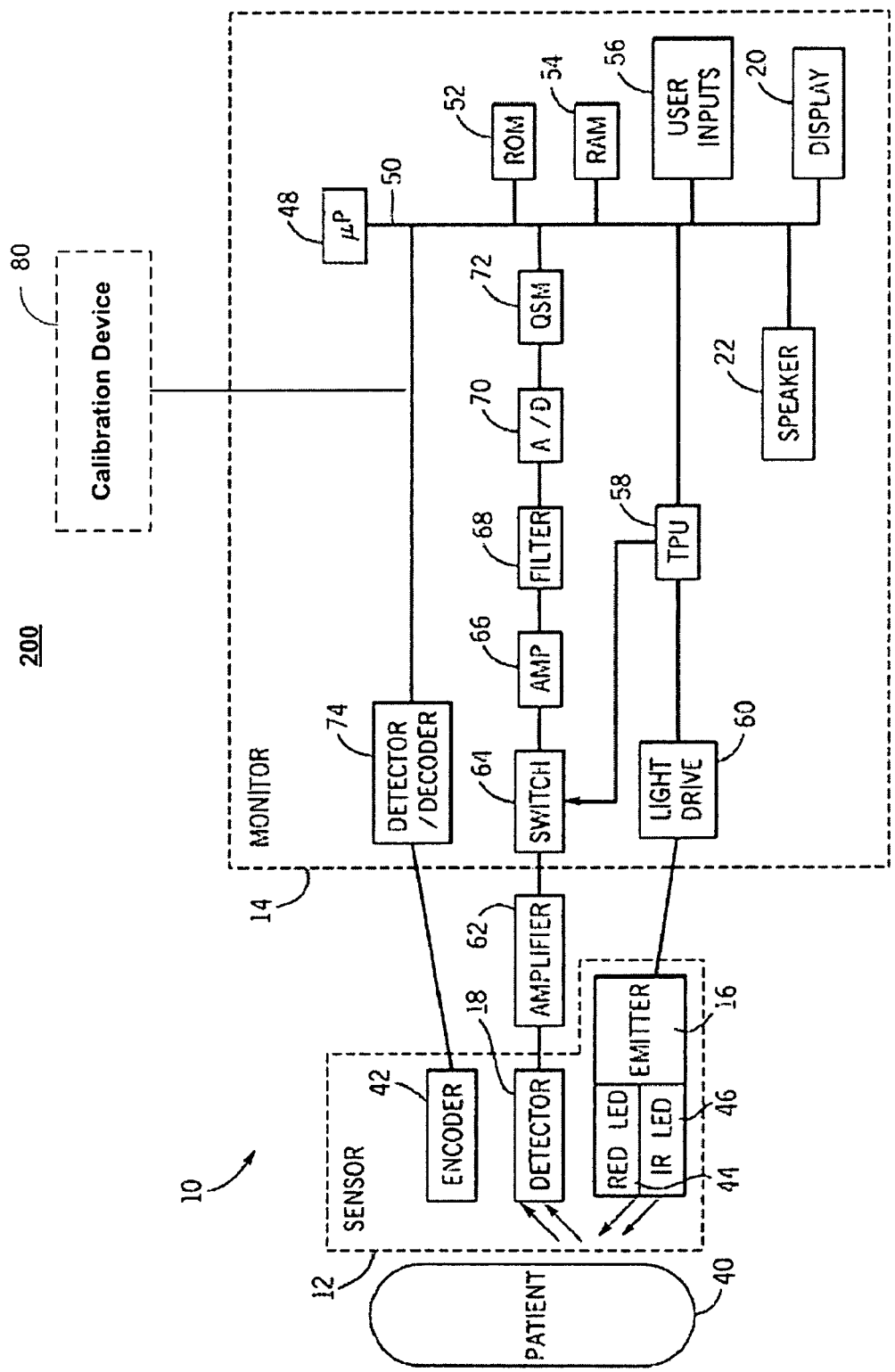
FIG. 2 is a block diagram of the illustrative CNIBP monitoring system of FIG. 1 coupled to a patient in accordance with an embodiment.

FIG. 2 is a block diagram of a CNIBP monitoring system, such as system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least one wavelength of light (e.g., RED or IR) into a patient's tissue 40. For calculating $SpO_2$, emitter 16 may include a RED light emitting light source such as RED light emitting diode (LED) 44 and an IR light emitting light source such as IR LED 46 for emitting light into the patient's tissue 40. In other embodiments, emitter 16 may include a light emitting light source of a wavelength other than RED or IR. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths (or any other suitable wavelength). Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of one or more of the RED and IR (or other suitable) wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. This information may also be used to select and provide coefficients for equations (associated with the empirical data) from which blood pressure is determined based on an area under a pulse of a PPG signal. Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelength or wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72

(or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as blood pressure, $SpO_2$, and pulse rate, using various algorithms and/or look-up tables based on the value of the received signals and/or data corresponding to the light received by detector 18. For example, microprocessor 48 may generate an equation that represents empirical data associated with one or more patients that includes various blood pressure measurements associated with different areas under a pulse of a PPG signal. Microprocessor 48 may compute an area under a pulse of a PPG signal (as discussed in more detail below) that is received from sensor 12. Microprocessor 48 may apply the computed area to the equation generated from the empirical data to determine blood pressure associated with patient 40. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the sensor or probe is attached.

Noise (e.g., from patient movement) can degrade a CNIBP or pulse oximetry signal relied upon by a physician, without the physician's awareness. This is especially true if the monitoring of the patient is remote, the motion is too small to be observed, or the doctor is watching the instrument or other parts of the patient, and not the sensor site. Processing CNIBP or pulse oximetry (i.e., PPG) signals may involve operations that reduce the amount of noise present in the signals or otherwise identify noise components in order to prevent them from affecting measurements of physiological parameters derived from the PPG signals.

CNIBP monitoring system 10 may also include calibration device 80. Although shown external to monitor 14 in the example of FIG. 2, calibration device 80 may additionally or alternatively be internal to monitor 14. Calibration device 80 may be connected to internal bus 50 of monitor 14. As described in more detail below, reference blood pressure measurements from calibration device 80 may be accessed by microprocessor 48 for use in calibrating the CNIBP measurements and determining blood pressure from an area under a pulse and empirical data of one or more patients.

Figure 3:
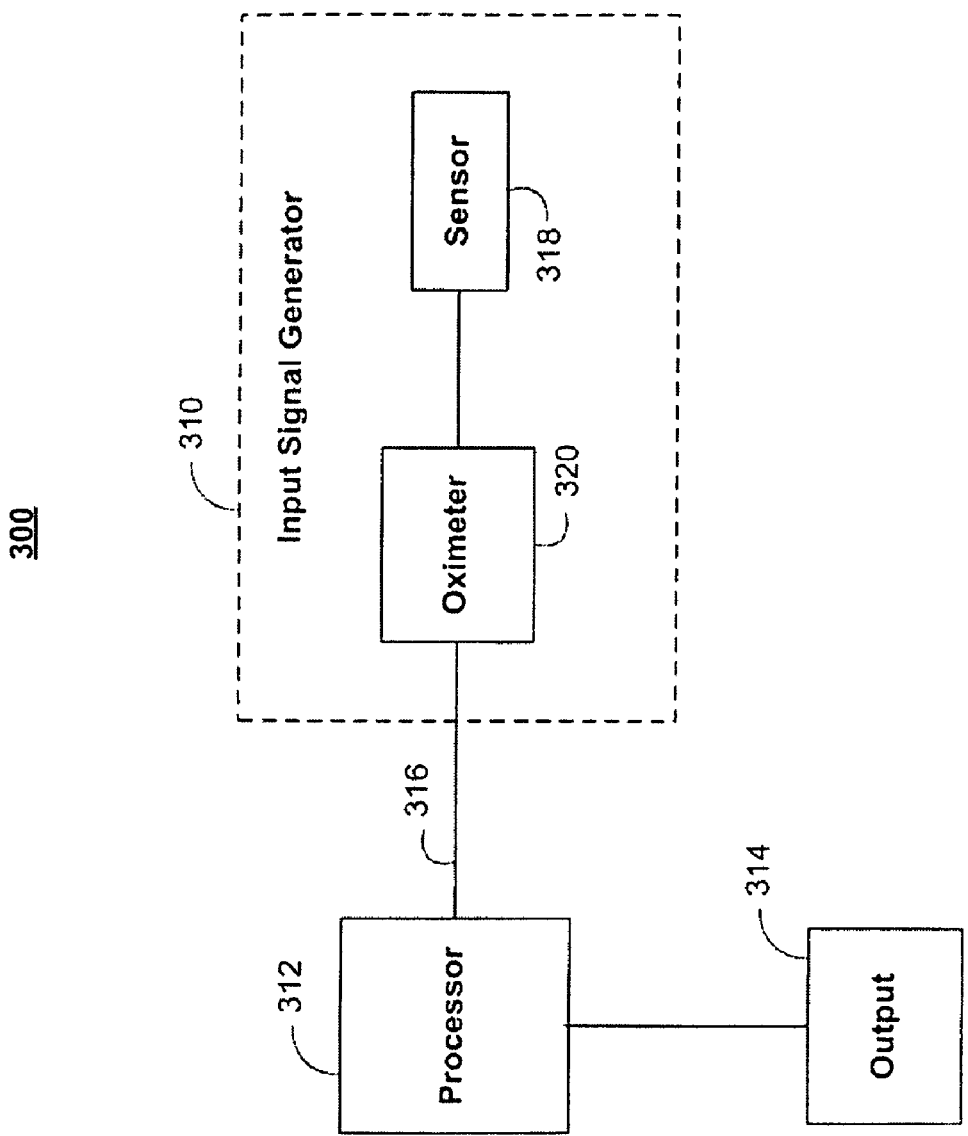
FIG. 3 is a block diagram of an illustrative signal processing system in accordance with some embodiments.

FIG. 3 is an illustrative processing system 300 in accordance with an embodiment. In an embodiment, input signal generator 310 generates an input signal 316. As illustrated, input signal generator 310 may include oximeter 320 (or similar device) coupled to sensor 318, which may provide as input signal 316, a PPG signal. It will be understood that input signal generator 310 may include any suitable signal source, signal generating data, signal generating equipment, or any combination thereof to produce signal 316.

In an embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform some or all of the calculations associated with the blood pressure monitoring methods of the present disclosure. For example, processor 312 may measure an area under a pulse of a PPG signal. Processor 312 may correlate the measured area with empirical data (e.g., blood pressure computations associated with different area measurements under a pulse) to determine blood pressure associated with the measured area. Processor 312 may also perform any suitable signal processing of signal 316 to filter signal 316, such as any suitable band-pass filtering, adaptive filtering, closed-loop filtering, and/or any other suitable filtering, and/or any combination thereof. For example, signal 316 may be filtered one or more times prior to or after identifying characteristic points in signal 316.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. Processor 312 may be coupled to a calibration device (not shown) that may generate or receive as input reference blood pressure measurements for use in calibrating CNIBP calculations.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor 12 and monitor 14 and processor 312 may be implemented as part of monitor 14. In some embodiments, portions of system 300 may be configured to be portable. For example, all or a part of system 300 may be embedded in a small, compact object carried with or attached to the patient (e.g., a watch (or other piece of jewelry) or cellular telephone). In such embodiments, a wireless transceiver (not shown) may also be included in system 300 to enable wireless communication with other components of system 10. As such, system 10 may be part of a fully portable and continuous blood pressure monitoring solution.

Figure 4:
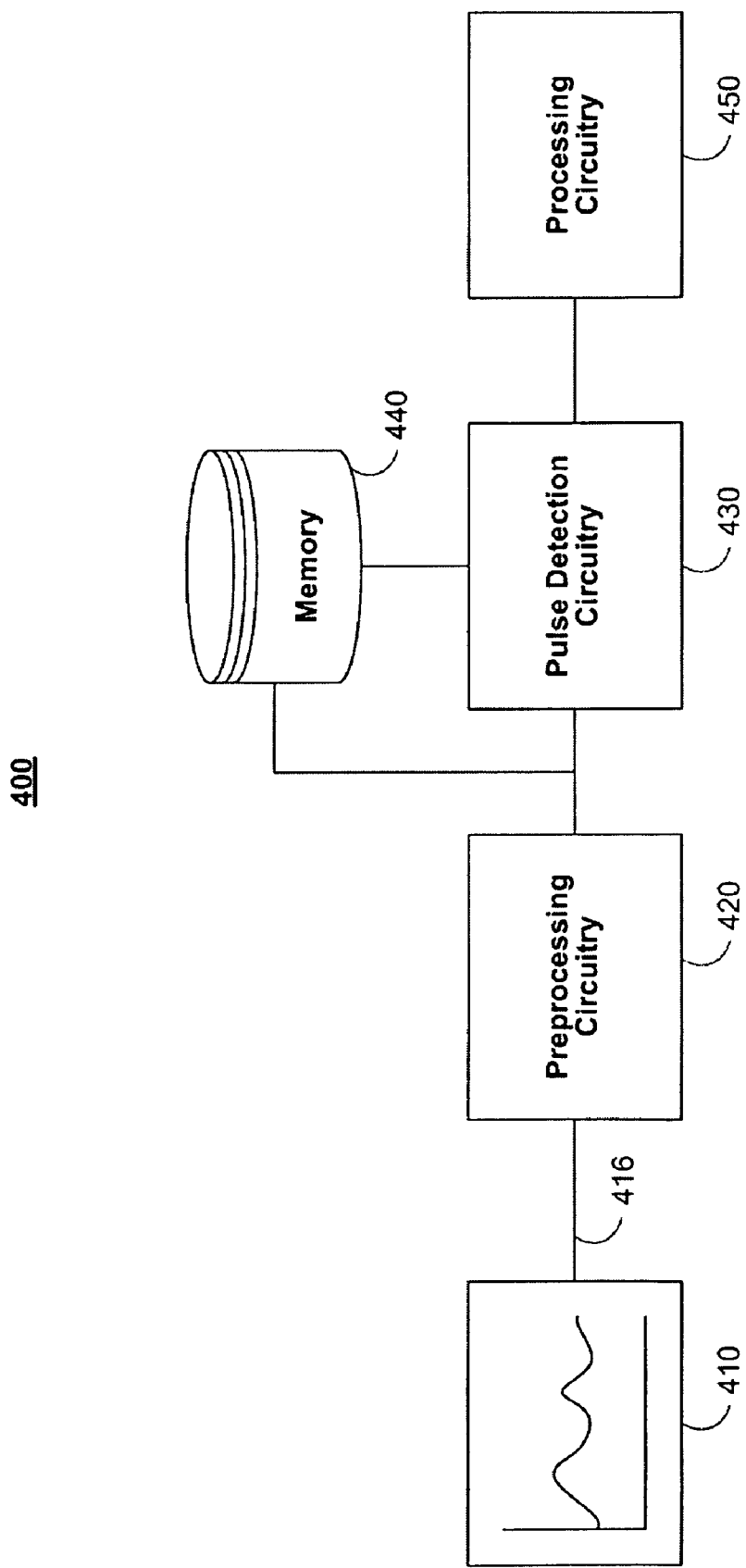
FIG. 4 is an illustrative embodiment of the systems of FIGS. 1-3 in accordance with some embodiments of the present disclosure.

FIG. 4 shows an illustrative embodiment of the systems of FIGS. 1-3 in accordance with some embodiments. PPG signal processing system 400 may include a PPG signal generation instrument 410 (e.g., sensor 12 (FIG. 2)), preprocessing circuitry 420 (e.g., filter 68), pulse detection circuitry 430, a memory 440 (e.g., ROM 52 or RAM 54) and processing circuitry 450 (microprocessor 48). It should be understood that although each component is drawn separately in FIG. 4, the components may be part of the same device or may be part of different devices in various combinations. For example, PPG signal generation instrument 410 and preprocessing circuitry 420 may be implemented by the same circuitry or device.

Input signal generation instrument 410 generates an input signal 416. Input signal generation instrument 410 may include an oximeter (not shown) coupled to sensor 12 (FIG. 2), which may provide a PPG signal as input signal 416. It will be understood that input signal generation instrument 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), or any combination thereof.

Signal 416 may be coupled to preprocessing circuitry 420. Preprocessing circuitry 420 may be any suitable software, hardware, or both for processing signal 416. For example, preprocessing circuitry 420 may include one or more hardware processors (e.g., integrated circuits), one or more software modules, memory, or any combination thereof. Preprocessing circuitry 420 may, for example, be a computer or may be one or more chips (i.e., integrated circuits). Preprocessing circuitry 420 may perform any suitable signal processing of signal 416 to filter signal 416, such as any suitable band-pass filtering, adaptive filtering, closed-loop filtering, any other suitable filtering, or any combination thereof. Filtering signal 416 may provide a cleaner, more workable version of the PPG signal by, for example, eliminating high frequency noise components that may be present in the PPG signal.

Figure 5:
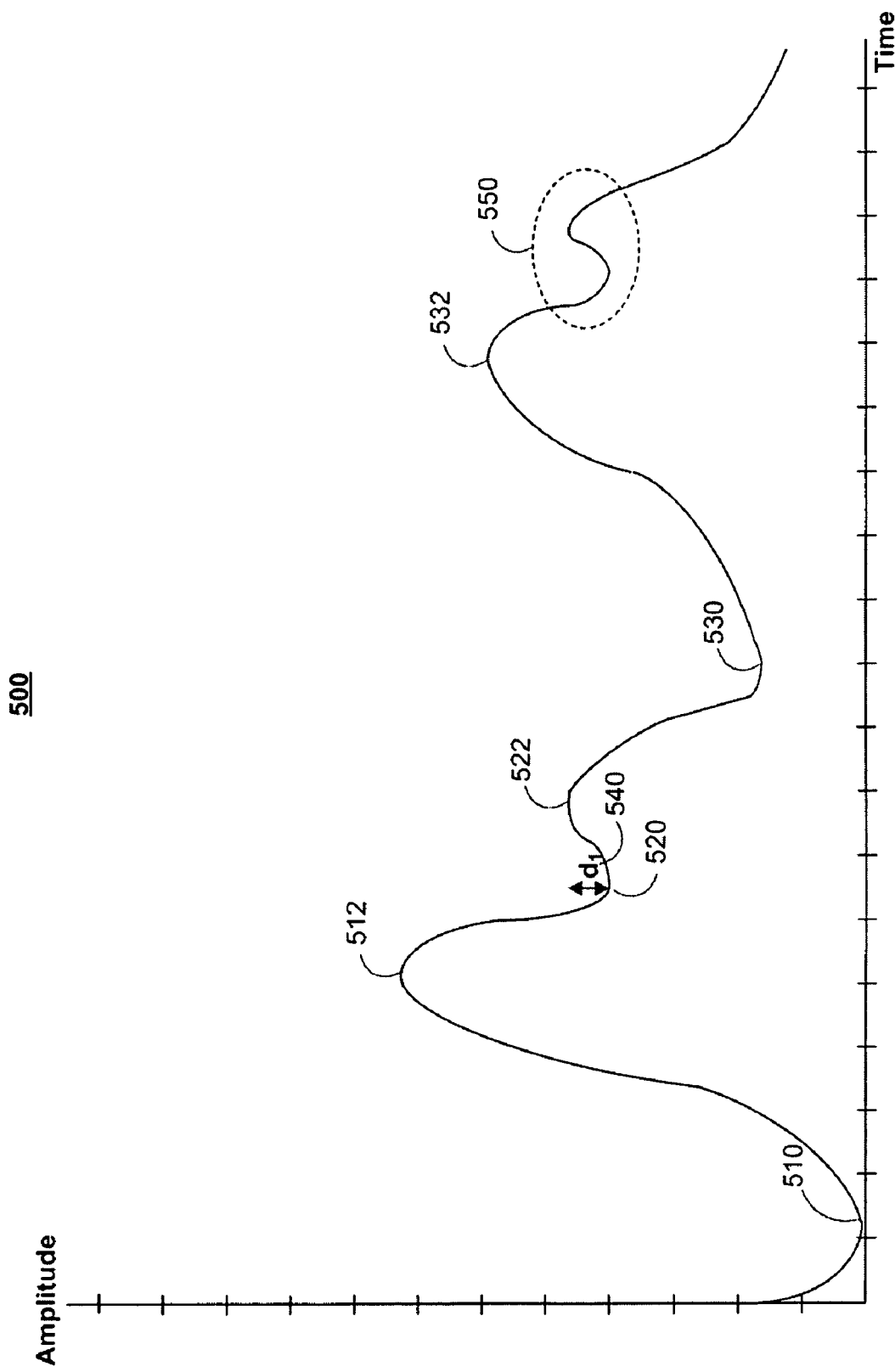
FIG. 5 shows an illustrative PPG signal in accordance with some embodiments of the present disclosure.

Preprocessing circuitry 420 may be coupled to pulse detection circuitry 430. Pulse detection circuitry 430 may determine the locations of pulses within the PPG signal. For example, as shown in FIG. 5, pulse detection circuitry 430 may receive PPG signal 500, according to an embodiment. Pulse detection circuitry 430 may identify a local minimum point 510, local maximum point 512, local minimum point 520, and local maximum point 522 in the PPG signal. Pulse detection circuitry 430 may pair each local minimum point with an adjacent maximum point. For example, pulse detection circuitry 430 may pair points 510 and 512 to identify one segment, points 512 and 520 to identify a second segment, points 520 and 522 to identify a third segment and points 522 and 530 to identify a fourth segment. The slope of each segment may be measured to determine whether the segment corresponds to an upstroke (e.g., a positive slope) or downstroke (e.g., a negative slope) portion of the pulse. The pulse is defined as a combination of at least one upstroke and one downstroke. For example, the segment identified by points 510 and 512 and the segment identified by points 512 and 520 may define a pulse.

According to an embodiment, PPG signal 500 may include a dichrotic notch 550 or other notches (not shown) in different sections of the pulse (e. g. at the beginning (referred to as an ankle notch), in the middle (referred to as a dichrotic notch), or near the top (referred to as a shoulder notch). Pulse detection circuitry 430 may identify notches and ignore them when detecting the pulse locations. in some embodiments, pulse detection circuitry 430 may compute the second derivative of the PPG signal to find the local minima and maxima points and may use this information to determine locations of, for example, a dichrotic notch. The techniques performed by pulse detection circuitry 430 are described in more detail in co-pending, commonly assigned U.S. patent application No. 12/242.908. filed Sep. 30, 2008, entitled "SYSTEMS AND METHODS FOR DETECTING PULSES," which is incorporated by reference herein in its entirety.

Processing circuitry 450 may be coupled to any suitable output device such as, for example, one or more medical devices (e.g., a medical monitor that displays various physiological parameters, a medical alarm, or any other suitable medical device that either displays physiological parameters or uses the output of preprocessing circuitry 420 as an input), one or more display devices 20 (FIG. 2) (e.g., monitor, PDA, mobile phone, any other suitable display device, or any combination thereof), one or more audio devices 22, one or more memory devices 52 or 54 (e.g., hard disk drive, flash memory, RAM, optical disk, any other suitable memory device, or any combination thereof), one or more printing devices, any other suitable output device, or any combination thereof.

Processing circuitry 450 may measure and compute one or more areas of the pulses detected by pulse detection circuitry 430. Processing circuitry 450 may measure the area by a suitable a mathematical function (e.g., an integration operation) to the pulse. Alternatively, processing circuitry 450 may measure the area by comparing the shape of a pulse area to a similar known shape (e.g., triangle, trapezoid, rectangle or circle) from which area can be computed. Processing circuitry 450 may use the measured areas to calculate the blood pressure. For example, processing circuitry 450 may use empirical data (e.g., by way of an equation that represents a patient among a class of patients in the empirical data) to determine a blood pressure associated with measured area. In particular, one patient may have an area that maps to one blood pressure while another patient may have the same area map to a different blood pressure (e.g., different patients may have different curves associated with their blood pressure-area mappings). Calibrating the system by way of calibration device 80 may enable processing circuitry 450 to select the equation or empirical data that is appropriate for the patient being examined. Processing circuitry 450 may alternatively perform a look-up of a particular area measurement in a table to determine a corresponding blood pressure.

FIGS. 6-10 show exemplary PPG signal pulse areas 600-1000B that may be computed by processing circuitry 450 in accordance with some embodiments. In particular, each pulse 600-1000B shows a different area that may be measured and used to determine blood pressure. Although only one pulse is shown and described below in the context of the disclosure, it should be understood that the areas of multiple pulses may be measured and used to determine blood pressure by, for example, using the median, maximum, minimum, average, or any other suitable function of multiple pulse area measurements.

Figure 6:
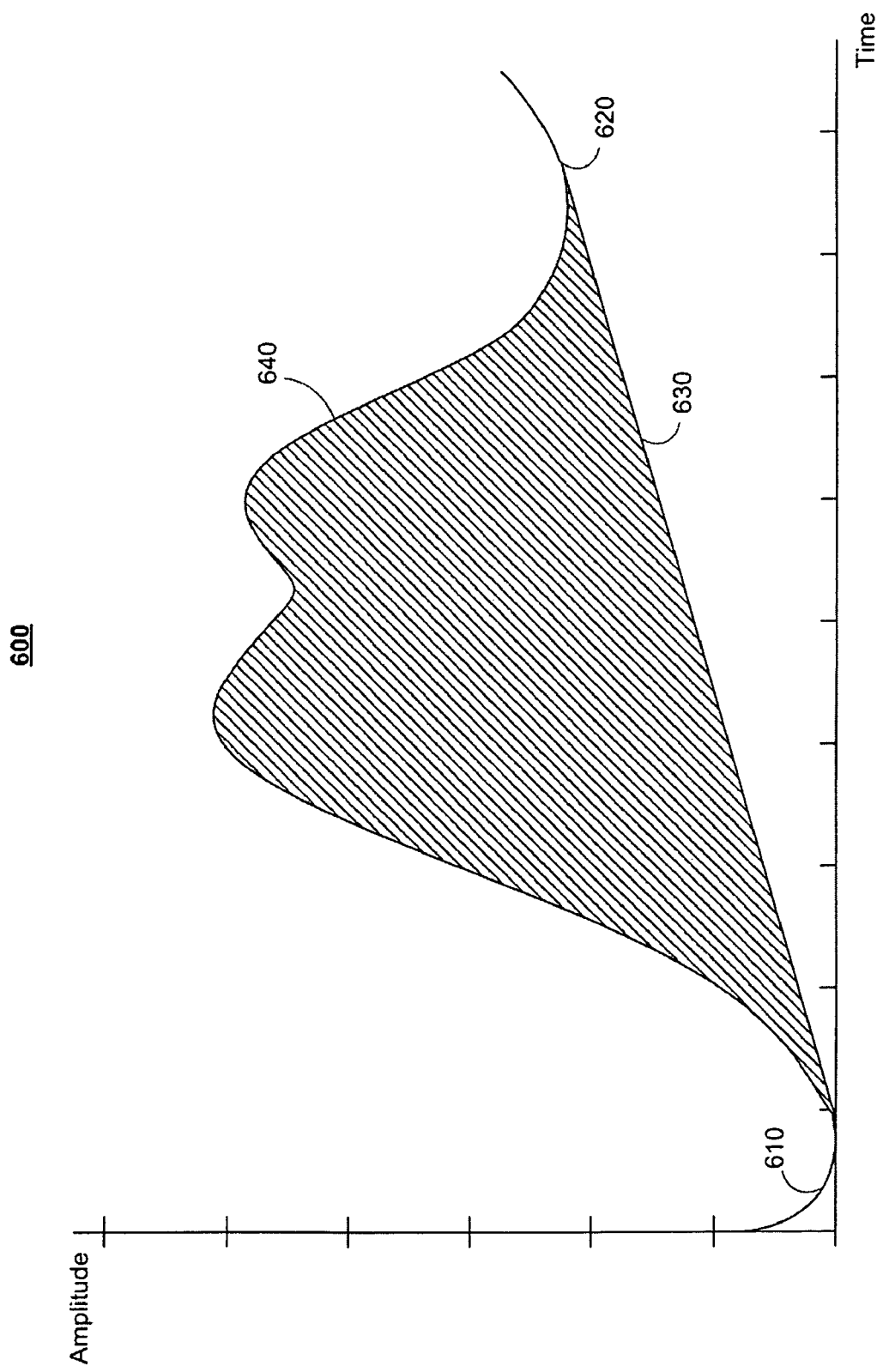
FIGS. 6, 7, 8, 9, 10A and 10B show illustrative pulse area measurements in accordance with some embodiments of the present disclosure.

In some embodiments, the area of a pulse may be measured relative to a baseline of the pulse. Pulse 600 is illustrative of an embodiment. Pulse 600 includes a starting point 610, an ending point 620 and a baseline 630 which is represented by a line segment connecting the starting and ending points of the pulse (FIG. 6). Area 640 may be the area of the entire pulse (between points 610 and 620) relative to baseline 630. The measured value of area 640 may be used to determine systolic and diastolic blood pressure. Processing circuitry 450 may be used to measure this area and compute blood pressure from the measured area. A similar area of one or more subsequent pulses may also be measured relative to baseline 630 or relative to their respective baselines. The mean, max, min, average or some other suitable value may be computed between the one or more areas (i.e., the area of the first pulse and the areas of one or more subsequent pulses). Processing circuitry 450 may use the mean, max, min, average or other suitable value that is computed to determine blood pressure.

Figure 7:
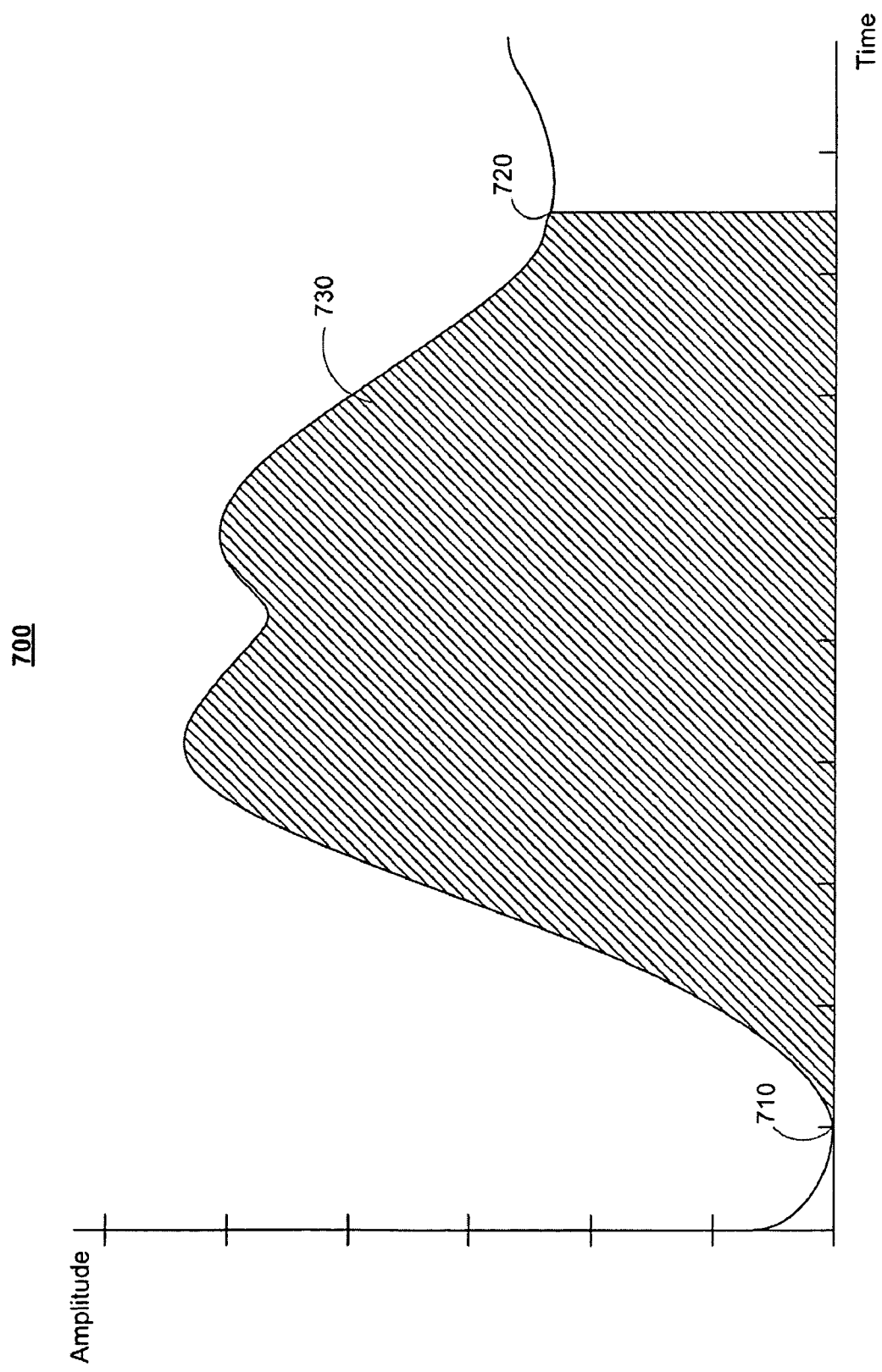

In some embodiments, the area of a PPG signal pulse may be measured relative to a time-domain axis. Pulse 700 is illustrative of an embodiment. Pulse 700 includes a starting point 710 and an ending point 720 (FIG. 7). Area 730 is the area of the entire pulse 700 (between points 710 and 720) relative to a constant valued baseline defined by a minimum value of the pulse or alternatively, the time-domain axis. A similar area of one or more subsequent pulses may be measured relative to similar, subsequently derived constant valued baseline. The mean, max, min, average or some other suitable value may be computed between the multiple areas (i.e., the area of the first pulse and the areas of one or more subsequent pulses) by processing circuitry 450. Processing circuitry 450 may use the mean, max, min, average or other suitable value that is computed to determine blood pressure.

In some embodiments, the area of an upstroke or downstroke of a PPG signal pulse may be measured relative to a constant valued baseline or time-domain axis of the pulse. Pulse 800 is illustrative of an embodiment. Pulse 800 includes a starting point 810, ending point 820 and maximum point 840. Area 830 of the pulse represents the area of the pulse corresponding to the upstroke of the pulse (e.g., the area between the starting point 810 of the pulse and the maximum point 840 of pulse 800 relative to a constant valued baseline with an amplitude value having the same value as point 810). Similarly, an area of the pulse corresponding to the downstroke of the pulse may be measured (e.g., the area between the maximum point 840 and the ending point 820 of pulse 800 relative to the constant valued baseline with an amplitude value having the same value as point 820). The area of one or more subsequent upstrokes or downstrokes of one or more pulses may also be measured relative to the similarly derived constant valued baseline. The mean, max, min, average or some other suitable value may be computed between the multiple areas (i.e., the area of the upstroke or downstroke of the first pulse and the areas of the upstrokes or downstrokes one or more subsequent pulses) by processing circuitry 450. Processing circuitry 450 may use the mean, max, min, average or other suitable value that is computed to determine blood pressure.

In some embodiments, the area of an upstroke or downstroke of the pulse may be measured relative to a baseline of the pulse. Pulse 900 is illustrative of an embodiment. Area 950 may be measured from the portion under pulse 900 between baseline 940, maximum point 930 and starting point 910. Area 950 may represent the area of the pulse corresponding to the upstroke of the pulse relative to the baseline. Similarly, an area of the pulse corresponding to the downstroke of the pulse may be measured for an area covered between the line extending from maximum point 930 and ending point 920. The area of one or more subsequent upstrokes or downstrokes of one or more pulses may also be measured relative to baseline 940 or their respective baselines. The mean, max, min, average or some other suitable value may be computed between the multiple areas (i.e., the area of the upstroke or downstroke of the first pulse and the areas of the upstrokes or downstrokes one or more subsequent pulses) by processing circuitry 450. Processing circuitry 450 may use the mean, max, min, average or other suitable value that is computed to determine blood pressure.

In some embodiments, a PPG signal pulse may be split into different sections and the area of each section may be used to determine either the systolic blood pressure or the diastolic blood pressure. For example, pulse 1000*a* is split into two sections. The pulse may be split along segment 1070 which may extend from an approximate midpoint of the upstroke of the pulse (a point between the starting point 1010 and maximum point 1060) to an approximate midpoint of the downstroke of the pulse (a point between maximum point 1060 and end point 1020).

Although segment 1070 extending from the midpoint is drawn parallel to baseline 1040, it should be understood that segment 1070 may be drawn at any angle relative to baseline 1040 without departing from the scope of this disclosure. It should also be understood, that although segment 1070 is shown and described as extending from the midpoint of the upstroke of the pulse, segment 1030 may extend from any point along the upstroke of the pulse to any point along the downstroke of the pulse to split the pulse into two sections. For example, the pulse may be split with a segment drawn from the starting point of a dichrotic or some other notch in the pulse parallel to the baseline or some with some other suitable slope. It should also be understood that the areas of each section of the split pulse may be measured relative to the time-domain axis as discussed above.

The area 1030 of a first section may be measured and the area 1050 of a second section may be measured. Area 1030 corresponding to the upper section of the pulse may be used to determine systolic blood pressure while area 1050 corresponding to the lower section of the pulse may be used to determine diastolic blood pressure. It should be understood that alternatively, the upper section may be used to determine diastolic blood pressure and the lower section may be used to determine systolic blood pressure.

In some embodiments, the pulse may be split into three sections and the areas of two of the three sections may be measured and used to determine blood pressure. For example, two segments may be drawn one extending from slightly above the midpoint and one extending from slightly below the midpoint forming an upper section and a lower section separated by a middle section. The areas of the upper section and lower sections may be used to determine blood pressure while the middle section may be ignored. Alternatively, any combination of two of the three sections may be measured and used to determine blood pressures The areas of multiple pulses and their respective sections may be similarly measured and a mean, median, average, maximum, or some other suitable value may be computed between the multiple respective areas. Processing circuitry 450 may use the mean, max, min, average or other suitable value that is computed to determine blood pressure.

Figure 10A:
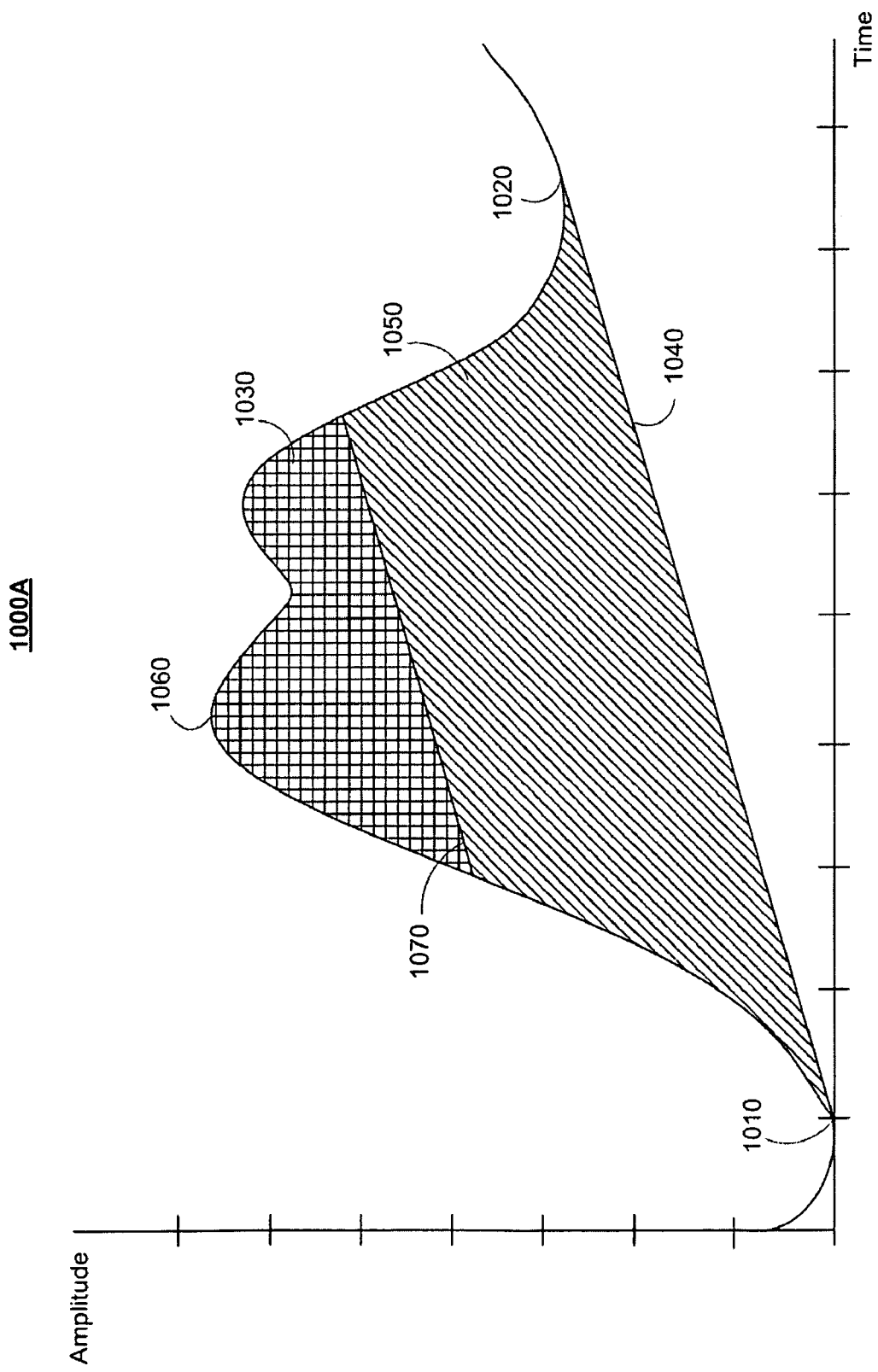
Figure 10B:
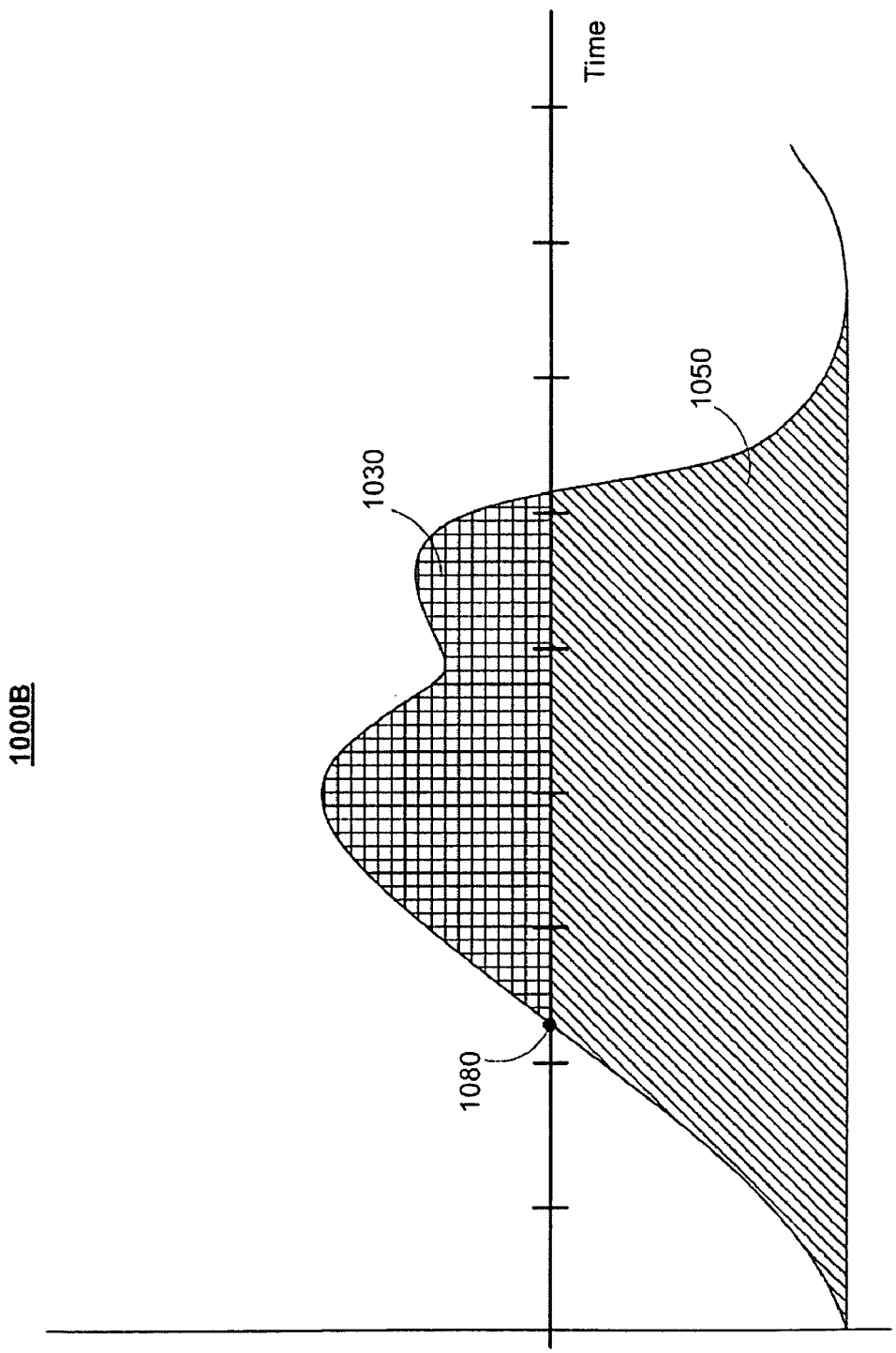

In some embodiments, pulse 1000B may be filtered such that the pulse is aligned along the time-domain axis as shown in FIG. 10B. In particular, a filter or some other suitable technique may be applied to pulse 1000B to cause the portion of the pulse that is above the segment 1080 (corresponding to segment 1070) extending from the midpoint of the pulse to be positioned above the time-domain axis (such that it corresponds to positive amplitudes) and the section below the midpoint to be positioned below the time-domain axis (such that it corresponds to negative amplitudes). The area of the upper pulse section may be measured and used to determine systolic blood pressure and the area of the lower pulse section may be measured and used to determine diastolic blood pressure. Alternatively, the area of the upper pulse section may be measured and used to determine diastolic blood pressure and the area of the lower pulse section may be measured and used to determine systolic blood pressure. This may simplify measuring areas of multiple pulses because all of the positive areas of the multiple pulses may correspond to the upper pulse sections and all of the negative areas of the multiple pulses may correspond to the lower pulse sections. A mean, max, median, min, or some other suitable value may more easily be computed from the multiple area measurements. Processing circuitry 450 may use the mean, max, min, average or other suitable value that is computed to determine blood pressure.

In some embodiments, the blood pressure may be determined from the measured area based on empirical data. For example, memory 440 (FIG. 4) may store values (samples taken by invasive or non-invasive blood pressure techniques) associated with one or more patients that map PPG signal pulse areas to blood pressure values. These are known as the empirical data. The empirical data may be based on previous blood pressure measurements of the patient currently being measured and/or blood pressure measurements of a particular group of patients.

Figure 11B:
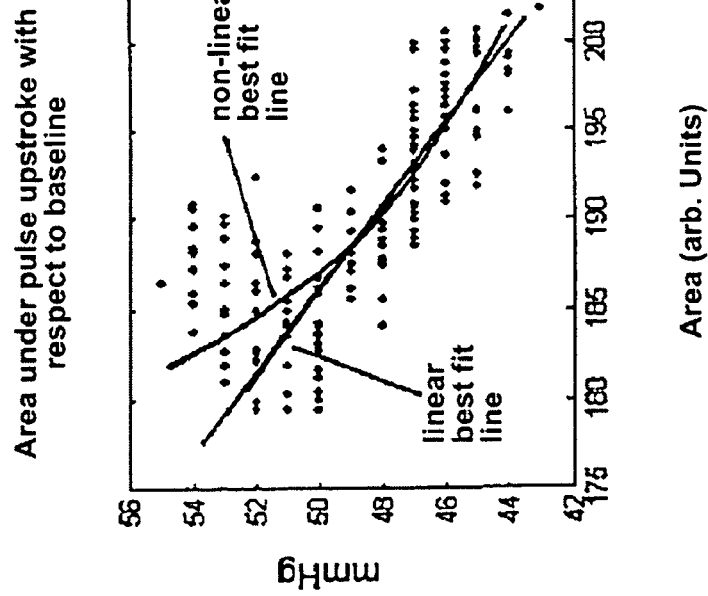
FIGS. 11A and 11B show illustrative empirical data in accordance with some embodiments of the present disclosure.
Figure 11A:
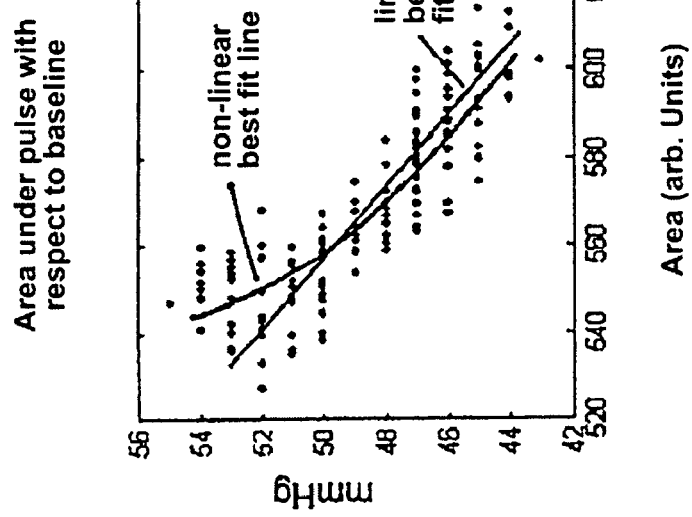

The empirical data stored in the memory may be used to derive an equation (e.g., a linear or non-linear best fit approximation) that represents a mapping of blood pressure to area measurement as shown in FIGS. 11*a*-*b*, according to embodiments. The equation may be derived by, for example, drawing a straight or curved line through the sample values that correspond to a particular class of patients. In particular, FIG. 11*a* shows blood pressure values for a particular patient versus pulse area values (in arbitrary units) corresponding to area 600 (FIG. 6) (entire pulse area relative to a baseline). FIG. 11*b* shows blood pressure values for a particular patient versus area values (in arbitrary units) corresponding to area 950 (FIG. 9) (pulse upstroke area relative to a baseline). Although FIGS. 11 and 11*b* show blood pressure values for a particular patient, values may similarly be provided on the graphs for multiple patients of a class or group of patients. More specifically, relationships between changes in area and blood pressure may be known and used to determine the particular blood pressure based on the measured area in question. In an alternative embodiment, blood pressure may be determined by looking up a particular area measurement in a table that maps areas to blood pressures. Performing a look-up to determine the blood pressure may make it unnecessary to compute the blood pressure through an equation or formula.

For example, empirical data for multiple patients can be used to determine a general relationship between blood pressure and area of a PPG signal pulse. The general relationship may be a linear equation with various coefficients. The linear equation may be used to determine the blood pressure of a patient used to form the equation or any other patient. An initial calibration may be performed on a particular patient to determine which linear or non-linear approximation applies to the particular patient and also to compute various coefficients of the equation which may be a linear or non-linear approximation of the empirical data.

The graphs shown in FIGS. 11*a* and 11*b* may be used to determine the blood pressure of a particular patient based on the measured area. For example, a PPG signal for a particular patient may be received. The pulse locations may be determined and the area under a portion or the entire pulse may be measured. In some embodiments, the actual blood pressure may be measured using known techniques in order to determine which of the approximations shown in FIGS. 11*a* and 11*b* are most appropriate to apply to the patient being measured. This is understood as the initial measurements that are used as the coefficients of the equations or functions that approximate the sample values shown in the graphs.

In particular, some patients may have an area that fits one blood pressure while others may have the same area fit a different blood pressure. These patients may form different groups and it may be necessary to determine to which group a particular patient being measured belongs. This may be done by comparing the actual blood pressure reading (received from known techniques such as using the auscultatory method, oscillometric method (automated NIBP), arterial line method, tonometric method, differential pulse transit time method or auscultation oscillometric method) with the area, or areas, measured corresponding to the particular patient. This comparison may be compared to data from other patients and used to identify a particular line approximation based on the patient group having the closest approximation.

For example, a patient being measured may have an actual blood pressure reading of 44 and an area measured to be 580. Looking at the graph (e.g., FIG. 11*a*), for an area of 580 there may be several different blood pressure readings and thus several linear or non-linear approximations. Accordingly, the approximation that is selected for future use for the patient being measured may be the approximation closest to the blood pressure reading of 44 with an area of 580. The coefficients may be derived corresponding to the approximation and used for future blood pressure determination based on area measurement without using known techniques such as the auscultatory method.

Although only two different types of graphs are shown in FIGS. 11*a* and 11*b*, it should be understood that any number of different graphs may be generated or used each corresponding to a different type of area measurement. For example, a graph may correspond to the area measurement of just the upstroke or downstroke relative to a baseline, another graph may correspond to the area measurement of just the upstroke or downstroke relative to an axis, another graph may correspond to the area measurement of the entire pulse relative to a baseline, and another graph may correspond to the area measurement of the entire pulse relative to an axis. As stated above, one graph or linear or non-linear approximation or equation may be used for determining diastolic blood pressure while another may be used to determine systolic blood pressure.

In an alternative embodiment, the relationship between measured areas and blood pressures may be derived using historical or empirical data. For example, the formulae for the lines of FIGS. 11*a* and 11*b* may be derived from historical data (e.g., arterial line data, pulse area data or calibration data). A line of choice may then be calculated for a particular subject from their area measurements in conjunction with pressures measured by calibration device 80. Continuous blood pressure may then be calculated from, for example, solely subsequently measured areas using the formula.

Figure 12:
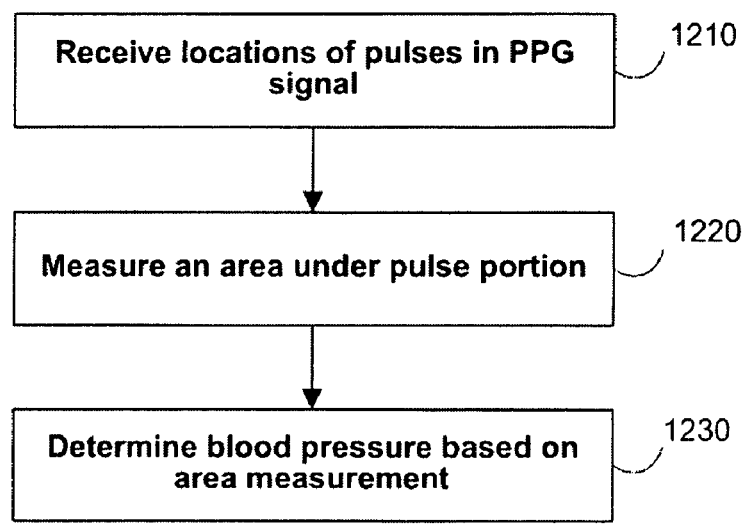
FIGS. 12 and 13 illustrate processes performed in accordance with some embodiments of the present disclosure.

FIG. 12 illustrates a process 1200 performed by processing circuitry 450 in accordance with some embodiments. The processes performed by processing circuitry 450 illustrated in FIG. 12 will be described with continued references to PPG signals 600-1000 (FIGS. 6-10).

At step 1210, locations of pulses in a PPG signal are received. For example, pulse detection circuitry 430 (FIG. 4) may provide to processing circuitry 450 the starting, ending, minimum and maximum points of each pulse, downstroke or upstroke in the PPG signal. Processing circuitry 450 may use this information to process and compute characteristics (e.g., area) of a particular pulse.

At step 1220, an area under a portion of a pulse is measured. For example, processing circuitry 450 may measure areas of different sections of the pulse in order to determine blood pressure. Some sections of the pulse may provide better correlation to blood pressure than others. Processing circuitry 450 may use the pulse locations received from pulse detection circuitry 430 to measure areas.

Figure 8:
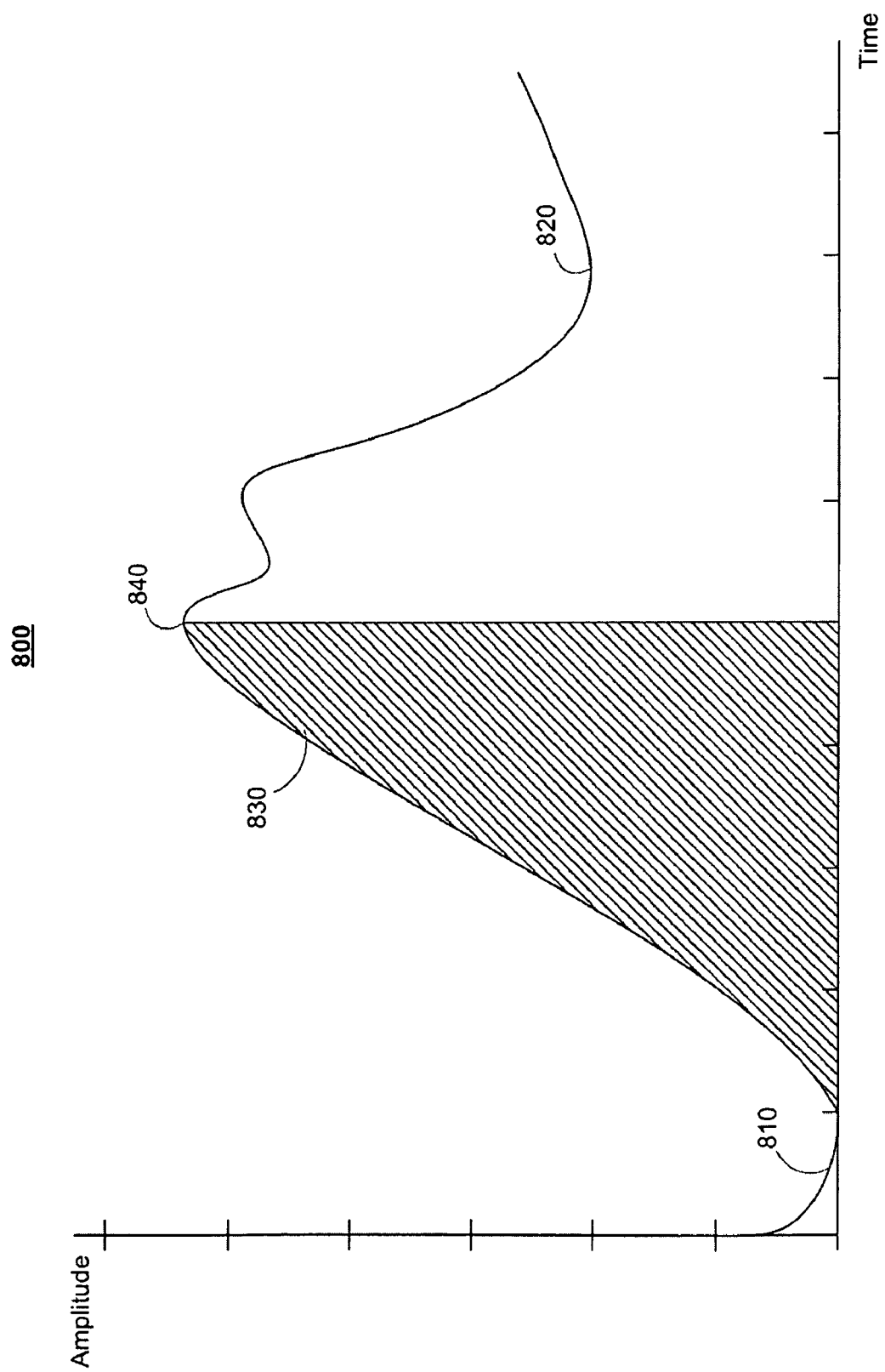
Figure 9:
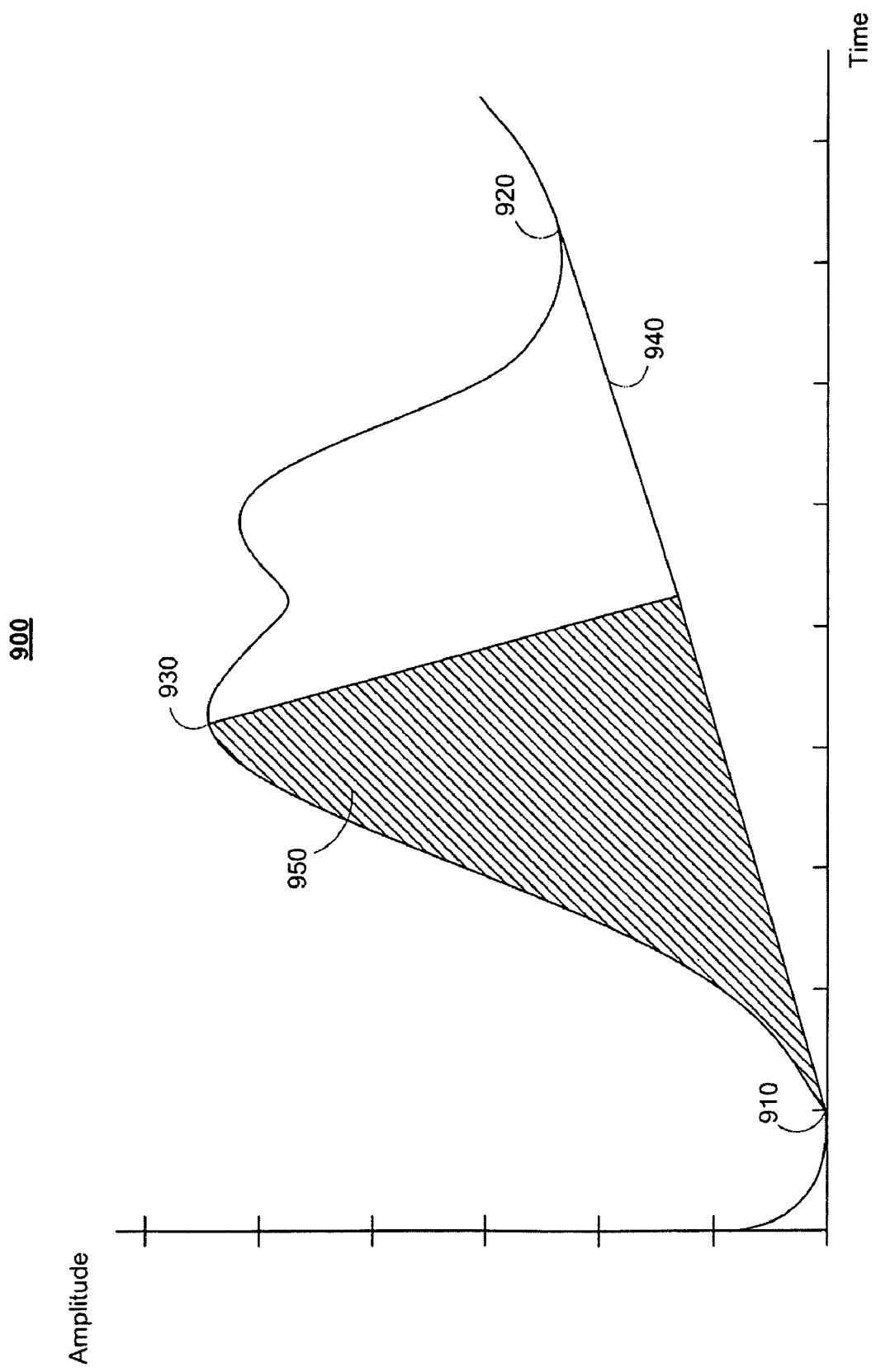

For example, in some embodiments, processing circuitry 450 may measure the area 640 of the entire pulse relative to baseline 630 (FIG. 6). In some embodiments, processing circuitry 450 may measure the area 730 of the entire pulse relative to the time-domain axis (e.g., x-axis) (FIG. 7). In some embodiments, processing circuitry 450 may measure area 830 of the upstroke portion of the pulse relative to the time-domain axis (e.g., x-axis) (FIG. 8). In some embodiments, processing circuitry 450 may measure area 950 of the upstroke or downstroke portion of the pulse relative to baseline 940 (FIG. 9). In some embodiments, processing circuitry 450 may measure two or more areas 1050 and 1030 of the pulse relative to baseline 1040 (FIGS. 10A and 10B).

At step 1230, blood pressure may be determined based at least in part on the measured area. Processing circuitry 450 may use the measured area to determine the blood pressure. In some embodiments, processing circuitry 450 may apply an equation or function (i.e., representing previously stored sample values to area mappings) to the measured area to determine blood pressure. Processing circuitry 450 may determine the blood pressure from the measured area based on empirical data. Alternatively, processing circuitry 450 may lookup the measured area in a predetermined table to find the corresponding blood pressure measurement.

It should also be understood that the area being measured may be in any arbitrary unit. It may be desired to have the unit used for measuring area for one patient be the same as the unit used for generating the linear or non-linear approximations.

It may be desirable to combine different area measurements to determine different blood pressures (e.g., systolic or diastolic). For example, it may be desirable to measure the area under the entire pulse to determine systolic blood pressure and measure the area just under the upstroke portion of the pulse to determine diastolic blood pressure. Alternatively, it may be desirable to measure the area under the entire pulse to determine diastolic blood pressure and measure the area just under the upstroke portion of the pulse to determine systolic blood pressure.

Figure 13:
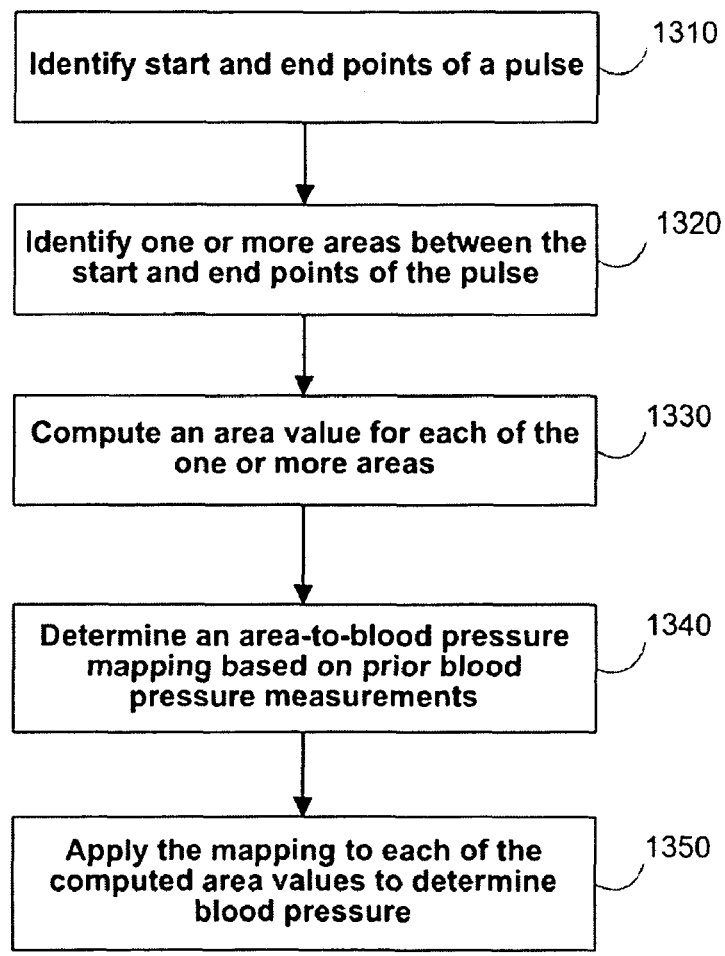

FIG. 13 illustrates a process 1300 performed by processing circuitry 450 in accordance with some embodiments. The processes performed by processing circuitry 450 illustrated in FIG. 13 will be described with continued references to PPG signals 600-1000 (FIGS. 6-10).

At step 1310, start and end points of a pulse are identified. For example, pulse detection circuitry 430 (FIG. 4) may provide to processing circuitry 450 starting point 610 and ending point 620 of pulse 600 in the PPG signal. Processing circuitry 450 may use this information to process and compute characteristics (e.g., area) of a particular pulse.

At step 1320, one or more areas between the start and end points of the pulse are identified. For example, processing circuitry 450 may identify area 640 of the entire pulse relative to baseline 630 (FIG. 6). In some embodiments, processing circuitry 450 may identify area 730 of the entire pulse relative to the time-domain axis (e.g., x-axis) (FIG. 7). In some embodiments, processing circuitry 450 may identify area 830 of the upstroke portion of the pulse relative to the time-domain axis (e.g., x-axis) (FIG. 8). In some embodiments, processing circuitry 450 may identify area 950 of the upstroke or downstroke portion of the pulse relative to baseline 940 (FIG. 9). In some embodiments, processing circuitry 450 may identify two or more areas 1050 and 1030 of the pulse relative to baseline 1040 (FIGS. 10A and 10B). In some implementations, the area identified by processing circuitry 450 may correspond to the systolic or diastolic blood pressure of a patient. Processing circuitry 450 may identify a particular area of interest depending on a desired blood pressure determination.

At step 1330, an area value is computed for each of the one or more areas. For example, processing circuitry 450 may compute an area of an upper portion, lower portion, or both relative to a time-domain or a baseline using, for example, integration techniques. Any other suitable geometric or trigonometric function or technique may be applied to measure the area of one or more sections of the pulse. The measured area value may be stored in memory 440 for later use (FIG. 4).

At step 1340, an area-to-blood pressure mapping is determined based on prior blood pressure measurements. For example, calibration device 80 may be used to sample or measure through invasive or non-invasive techniques actual blood pressure for one or more patients and a corresponding area of a particular pulse (FIG. 2). The blood pressure measured by calibration device 80 and corresponding pulse area may be stored in RAM 52 or ROM 54 and may be mapped to a graph (e.g., FIGS. 11A and 11B). Processing circuitry 450 may generate an equation or function that represents the samples measured by calibration device 80 (e.g., a straight-line, linear or non-linear approximation) (FIG. 2).

Additionally, calibration device 80 may be used to measure any necessary coefficient values in the equation or function. For example, one equation or function may be better suited for one class of patients than another. Accordingly, calibration device 80 may provide coefficients to processing circuitry 450 in order to make the equation or function more appropriate to a particular patient. Alternatively, processing circuitry 450 generate a table that represents the mapping of the blood pressures and areas measured or sampled by calibration device 80 and store the table in memory 440 (FIG. 4).

At step 1350, the mapping is applied to each of the computed area values to determine blood pressure. For example, processing circuitry 450 may retrieve one of the functions or equations from the memory and apply the computed areas to the functions or equations to determine the blood pressure(s) that corresponds to the computed area(s). Alternatively, processing circuitry 450 may look up in a stored table a particular computed area and determine the corresponding blood pressure measurement.

The foregoing is merely illustrative of the principles of this disclosure and various modifications can be made by those skilled in the art without departing from the scope and spirit of the disclosure. The following numbered paragraphs may also describe various aspects of the disclosure.

What is claimed is:
1. A method of determining blood pressure based on a PPG signal, the method comprising;
  receiving locations of pulses in the PPG signal;
  measuring an area under a portion of one of the pulses, wherein:
    the portion is smaller than a region occupied by the pulse between a starting point and ending point of the pulse, and
    the measured area is an area under the pulse between the starting point of the pulse to the ending point of the pulse relative to a baseline of the pulse; and
  determining blood pressure based on the measured area.
2. A method of determining blood pressure based on a PPG signal, the method comprising:
  receiving locations of pulses in the PPG signal;

measuring an area under a portion of one of the pulses, wherein:
  the portion is smaller than a region occupied by the pulse between a starting point and ending point of the pulse, and
  the measured area is an area under the pulse between the starting point of the pulse to the ending point of the pulse relative to a temporal axis; and
determining blood pressure based on the measured area.

3. The method of claim 1, wherein the measured area is an area under an upstroke portion of the pulse relative to a baseline of the pulse.

4. The method of claim 2 wherein the measured area is an area under an upstroke portion of the pulse relative to a temporal axis.

5. A method of determining blood pressure based on a PPG signal, the method comprising:
  receiving locations of pulses in the PPG signal:
  measuring an area under a portion of one of the pulses, wherein measuring an area under the pulse comprises:
    splitting the pulse along the temporal axis;
    measuring a first area corresponding to a first portion of the split pulse, wherein the first portion is smaller than a region occupied by the pulse between a starting point and ending point of the pulse;
    measuring a second area corresponding to a second portion of the split pulse, wherein the second portion is smaller than a region occupied by the pulse between a starting point and ending point of the pulse; and
  determining the blood pressure based on one of the measure areas.

6. The method of claim 1 wherein determining blood pressure based on the measured area comprises correlating the measured area with empirical data.

7. The method of claim 6 wherein the empirical data relates to a patient or at least one other patient.

8. The method of claim 6 wherein correlating the measured area with empirical data comprises applying a linear or non-linear approximation equation of empirical data to the measured area.

9. The method of claim 8 wherein the linear or non-linear approximation equation is derived by applying calibration data.

10. The method of claim 1 wherein the blood pressure is determined by applying a function to the measured area to compute the blood pressure or looking up a corresponding blood pressure value associated with the measured area in a table.

11. A system for determining blood pressure based on a PPG signal, the system comprising:
  processing circuitry capable of:
    receiving locations of pulses in the PPG signal;
    measuring an area under a portion of one of the pulses, wherein:
      the portion is smaller than a region occupied by the pulse between a starting point and ending point of the pulse, and
      the measured area is an area under the pulse between the starting point of the pulse to the ending point of the pulse relative to a baseline of the pulse; and
    determining blood pressure based on the measured area.

12. A system for determining blood pressure based on a PPG signal, the system comprising:
  processing circuitry capable of:
    receiving locations of pulses in the PPG signal:
    measuring an area under a portion of one of the pulses, wherein:
      the portion is smaller than a region occupied by the pulse between a starting point and ending point of the pulse, and
      the measured area is an area under the pulse between the starting point of the pulse to the ending point of the pulse relative to a temporal axis; and
    determining blood pressure based on the measured area.

13. The system of claim 11 wherein the measured area is an area under an upstroke portion of the pulse relative to a baseline of the pulse.

14. The system of claim 12 wherein the measured area is an area under an upstroke portion of the pulse relative to a temporal axis.

15. A system for determining blood pressure based on a PPG signal, the system comprising:
  processing circuitry capable of:
    receiving locations of pulses in the PPG signal;
    measuring an area under a portion of one of the pulses, wherein measuring an area under the pulse comprises:
      splitting the pulse along the temporal axis;
      measuring a first area corresponding to a first portion of the split pulse, wherein e first portion is smaller than a region occupied by the pulse between a starting point and ending point of the pulse;
      measuring a second area corresponding to a second portion of the split pulse, wherein the second portion is smaller than a region occupied by the pulse between a starting point and ending point of the pulse; and
    determining the blood pressure based on one of the measured areas.

16. The system of claim 11 wherein the processing circuitry is further capable of correlating the measured area with empirical data.

17. The system of claim 16 wherein the empirical data relates to a patient or at least one other patient.

18. The system of claim 16 wherein the processing circuitry is further capable of applying a linear or non-linear approximation equation of empirical data to the measured area.

19. The system of claim 18 wherein the linear or non-linear approximation equation is derived by applying calibration data.

20. The system of claim 11 wherein the blood pressure is determined by applying a function to the measured area to compute the blood pressure or looking up a corresponding blood pressure value associated with the measured area in a table.

* * * * *